United States Patent [19]
Makovec et al.

[11] Patent Number: 5,985,885
[45] Date of Patent: Nov. 16, 1999

[54] QUINAZOLINE-4-AMINO-2-(PIPERIDINE-1-YL-4-SUBSTITUTED) DERIVATIVES HAVING ANTIHYPERTENSIVE ACTIVITY, A METHOD FOR THEIR PREPARATION AND THEIR PHARMACEUTICAL USE

[75] Inventors: Francesco Makovec, Monza; Walter Peris, Milan; Lucio Claudio Rovati; Luigi Angelo Rovati, both of Monza, all of Italy

[73] Assignee: Rotta Research Laboratorium S.p.A., Milan, Italy

[21] Appl. No.: 09/155,993

[22] PCT Filed: Jul. 31, 1996

[86] PCT No.: PCT/EP96/03370

§ 371 Date: Oct. 9, 1998

§ 102(e) Date: Oct. 9, 1998

[87] PCT Pub. No.: WO97/37979

PCT Pub. Date: Oct. 16, 1997

[30] Foreign Application Priority Data

Apr. 10, 1996 [IT] Italy ................. TO96A0275

[51] Int. Cl.$^6$ ............. A61K 31/505; C07D 401/14; C07D 405/14
[52] U.S. Cl. ............. 514/260; 544/284; 544/291
[58] Field of Search ............. 514/260; 544/284, 544/291

[56] References Cited

U.S. PATENT DOCUMENTS

| | | | |
|---|---|---|---|
| 3,511,836 | 5/1970 | Hess | 544/291 |
| 3,960,861 | 6/1976 | Danilewicz | 544/291 |
| 5,798,362 | 8/1998 | Leonardi | 544/291 |

FOREIGN PATENT DOCUMENTS

| | | |
|---|---|---|
| 028473 | 5/1981 | European Pat. Off. . |
| 039190 | 11/1981 | European Pat. Off. . |
| 055583 | 7/1982 | European Pat. Off. . |
| 139993 | 5/1985 | European Pat. Off. . |
| 188094 | 7/1986 | European Pat. Off. . |
| 94/05628 | 3/1994 | WIPO . |
| 95/25726 | 9/1995 | WIPO . |

OTHER PUBLICATIONS

Campbell, S.F., and Plews, R.M. J. Med. Chem. 30, 1794–1798, 1987.

*Primary Examiner*—Mukund J. Shah
*Assistant Examiner*—V Balasubramanian
*Attorney, Agent, or Firm*—Sughrue, Mion, Zinn, Macpeak & Seas, PLLC

[57] ABSTRACT

New quinazolines are described of general formula (I), in which Ar is an unsubstituted phenyl group or a phenyl group mono-substituted with a methoxy, ethoxy or methyl group; an unsubstituted pyridyl group (2-, 3- or 4-yl) or a pyridyl group mono-substituted with a methoxy or methyl group; an unsubstituted furyl group (2- or 3-yl) or a furyl group substituted with a methoxy or methyl group; a benzofuryl group (2- or 3-yl); an indolyl group (2- or 3-yl); a thiophenyl group (2- or 3-yl); a naphthyl group (1- or 2-yl) and their salts obtained from pharmaceutically acceptable inorganic or organic acids.

These new quinazolines are useful in the treatment of hypertension, congestive heart failure, prostate hypertrophy, various urinary tract disorders and pathological symptoms caused by hyperactivity or disfunctioning of the noradrenergic neural system.

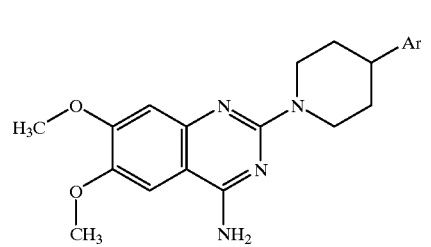

12 Claims, No Drawings

QUINAZOLINE-4-AMINO-2-(PIPERIDINE-1-YL-4-SUBSTITUTED) DERIVATIVES HAVING ANTIHYPERTENSIVE ACTIVITY, A METHOD FOR THEIR PREPARATION AND THEIR PHARMACEUTICAL USE

BACKGROUND OF THE INVENTION

1. Field of the Invention

The present invention relates to 2-piperidine (4-substituted) derivatives of 4-amino-6,7-dimethoxyquinazolines. These compounds are useful in the treatment of hypertension, congestive heart failure, prostate hypertrophy, various urinary tract disorders and pathological symptoms caused by hyperactivity or dysfunctioning of the noradrenergic neural system.

2. Description of the Related Art

The hypotensive activity of a variety of quinazoline-piperazine derivatives is well known. For example, U.S. Pat. No. 3,511,836 describes the hypotensive activity of 4-amino-6,7-dialkoxy-2-(piperazine-(4-substituted)-1-yl) quinazolines, in which the substituent in the 4-position of the piperazine is a benzoyl or furyl group; U.S. Pat. No. 4,001,237 describes the hypotensive activity of analogous derivatives in which the 4-substituent is an oxazolyl, thiazolyl, isoxazolyl or isothiazolyl group; U.S. Pat. No. 4,188,390 describes the hypotensive activity of analogous derivatives in which the 4-substituent is, inter alia, a group such as 1,4-benzodioxan-2-carbonyl.

BRIEF SUMMARY OF THE INVENTION

The subject of the invention is new 2-piperidine(4-substituted) derivatives of 4-amino-6,7-dimethoxy-quinazoline which may be represented by the general formula (I) indicated below

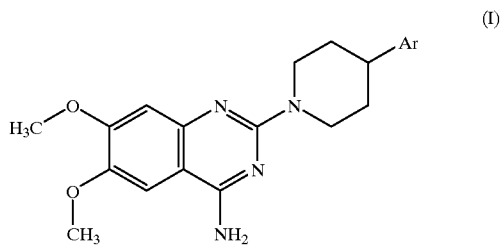

in which:
Ar is
an unsubstituted phenyl group or a phenyl group mono-substituted with a methoxy, ethoxy or methyl group
an unsubstituted pyridyl group (2-, 3- or 4-yl) or a pyridyl group mono-substituted with a methoxy or methyl group
an unsubstituted furyl group (2- or 3-yl) or a furyl group substituted with a methoxy or methyl group
a benzofuryl group (2- or 3-yl)
an indolyl group (2- or 3-yl)
a thiophenyl group (2- or 3-yl)
a naphthyl group (1- or 2-yl)

The compounds of the present invention have been shown to be powerful antagonists to noradrenergic receptors (alpha$_{1A}$ and alpha$_{1B}$ receptor subtypes) and serotonergic receptors, and can therefore be used to advantage in treating various human illnesses, whether at the level of the cardiovascular system, in particular for treating hypertension, as well as in the urogenital apparatus, for example, in the treatment of prostate hypertrophy, various urinary tract problems and, in general, the pathological manifestations caused by hyperactive or disfunctioning adrenergic receptors.

DETAILED DESCRIPTION OF THE INVENTION

One of the advantages of the new piperidine-quinazoline derivatives of the invention over previously known piperazine-quinazoline compounds having hypotensive activity is that, as they do not contain the piperazine nucleus in their chemical structure, their use should eliminate the potential danger of neurotoxic manifestations in patients with renal failure or central nervous system disorders.

A further advantage is the absence from their chemical structure of the carbonyl-piperazine bond which is susceptible to in vivo enzymatic hydrolysis. In effect, compounds with a high bioavailability and duration of action are obtained. This allows the therapeutic dose to be reduced, for a given effectiveness and, consequently, any undesirable side-effects will be reduced.

In addition to the powerful hypotensive effect demonstrated by the compounds of the invention linked to the blocking of the alpha$_1$ adrenergic receptor, they can also display an antagonistic effect on seratonin receptors which are widely present in some peripheral tissues such as the vascular musculature and the thrombocytes, thereby also blocking the amplification effect of seratonin on the vasoconstrictive and thrombocytic-aggregation activity of catecholamines.

Pharmaceutical forms of the compounds of the invention may be prepared by conventional techniques in the form of, for example, tablets, capsules, suspensions, solutions, suppositories or patches, and may be administered orally, parenterally, rectally or transdermally, or in other suitable ways to obtain the therapeutic effect such as, for example, as solid preparations for oral use having a protracted action which allow the controlled release of the active ingredient over time.

The active ingredient is usually administered to the patient in a reference dose which may vary from 0.001 to 1 mg/kg bodyweight per dose. In the case of parenteral administration it is preferable to use a hydrosoluble salt of the compound in question such as the hydrochloride or another non-toxic, pharmaceutically acceptable salt. The inactive ingredients may be substances that are commonly used in pharmaceutical preparations such as excipients, binders, aromatisers, dispersents, colorants, humectants etc.

The method for the preparation of the derivatives of the invention (I) consists of reacting the piperidine derivatives of the formula (II):

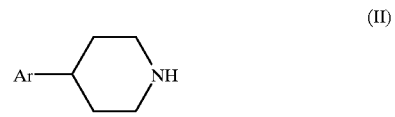

in which Ar has the meaning indicated above, with 2-Cl-4-amino-6,7-dimethoxy quinazoline in a solvent with a high boiling point, preferably isoamyl alcohol, in the presence or absence of an inert tertiary base which acts as a proton acceptor, at a temperature of 70–150° C. for a period of 1–48 hours, and isolating the compounds of formula (I) from the reaction medium by filtration, preferably in the form of the hydrochloride.

The intermediate piperidines of formula (II) used in the present invention, some of which are compounds which are already known, were prepared in a similar manner to that described in U.S. Pat. No. 2891066. This method consists of a series of reactions comprising:

a) reacting the aromatic aldehydes Ar—CHO, in which Ar has the meaning given above, with ethyl acetoacetate to give the compound of formula (III):

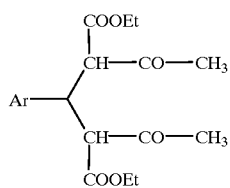

b) hydrolysing the compound of formula (III) with NaOH to give the glutaric derivative of formula (IV):

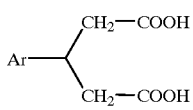

c) treating (IV) with excess ammonia at high temperature to give the imides of formula (V):

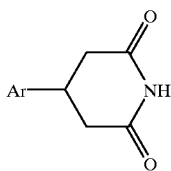

d) reducing the imides (V) with $LiAlH_4$ to give the desired piperidines of formula (II).

The following examples are given to illustrate the invention better.

EXAMPLE 1

Preparation of 4-(2-pyridyl)-bis-ethyl acetoacetate (Compound A of Formula III)

30 ml of ethanol, 50 ml of 2-pyridylcarboxyaldehyde (0.5256 moles), 133 ml of ethyl acetoacetate (1.0513 moles) and 10.4 ml of piperidine (0.1051 moles) were mixed in sequence.

At the end of the addition, the reaction was allowed to proceed under agitation at 35–40° C. for 8 hours. The solvents and the reactants were evaporated under vacuum, 166 g of a dark, non-friable oily residue being obtained.

Formula: $C_{18}H_{23}NO_6$. Yield: 0.475 moles (90%)
TLC: Rf 0.20 (toluene/AcOEt 7:3).

The compound was used without further purification in the next reaction.

EXAMPLE 2

Preparation of 3-(2-pyridyl)glutaric acid (hydrochloride)
(Compound B of Formula IV)

166 g of Compound A (Example 1) (0.475 moles) were added dropwise to a solution containing 800 ml of ethanol and 290 g of 65% NaOH in $H_2O$ (4.7303 moles). At the end of the dropwise addition the reaction was allowed to proceed at boiling point for approximately 2 hours. After cooling, the paste-like residue formed was taken up with 400 ml of isopropyl alcohol and filtered. The solid was dissolved in 500 ml $H_2O$ and, after cooling, the solution obtained was acidified with 37% HCl. The acidic solution was evaporated to dryness under vacuum, the residue was taken up in methanol and the solid precipitate (NaCl) was discarded. The methanolic solution was evaporated to dryness and gave 74 g of a dense, non-friable oil which was used as such in the next step.

Formula: $C_{10}H_{11}NO_4.HCl$. Yield: 0.301 moles (63%)
TLC: Rf 0.49 (n-BuOH/acetic A./$H_2O$ 5:2:2).

EXAMPLE 3

Preparation of 3-(2-pyridyl)-glutarimide (Compound C of Formula V)

70 g of 3-(2-pyridyl)glutaric acid hydrochloride (Compound B) (0.2489 moles) were dissolved in 80 ml of 28% ammonia (1.1398 moles). This was heated under agitation to 80° C., when most of the excess ammonia evaporated. The $H_2O$ also evaporated when the temperature reached 100–110° C. The resulting semi-solid viscous mass was then heated to 180° C. at which point the ammonia was completely eliminated. Once the evolution of ammonia ceased, the reaction mixture was cooled and the residue was taken up in ethyl acetate and was washed with $NaHCO_3$ to remove unreacted (B). The organic phase was then washed with water, dried and evaporated. The solid residue obtained was taken up in isopropyl ether and filtered. 32 g of product (C) were obtained after dessication.

Formula: $C_{10}H_{10}N_2O_2$. Yield: 0.1682 moles (59%)
TLC: Rf 0.62 (MeOH/AcOEt 9:1)
Melting point: 126–127° C.

EXAMPLE 4

Preparation of 4-(2-pyridyl)-piperidine (Compound D of Formula II)

25 g of $LiAlH_4$ (0.63 moles) were suspended in 600 ml anhydrous tetrahydrofuran (THF). The suspension was heated to 40° C. and, at this temperature, 30 g of 3-(2-piridyl)-glutarimide (Compound C) (0.1578 moles) were added gradually.

The mixture was heated under reflux for 12 hours. It was then cooled to −10° C. and, still under cooling, was hydrolysed by the sequential addition of 25 ml $H_2O$, 25 ml 30% NaOH and 50 ml of $H_2O$. The mixture was left to rest for several hours and then the salts were filtered off and the THF solution evaporated to dryness under vacuum. The oily residue was dissolved in ether and converted to the hydrochloride by treatment with gaseous HCl. After dessication, 26 g of a pale pink solid was obtained (Compound D) which, being hygroscopic, was used as soon as possible.

Formula: $C_{10}H_{14}N_2.2HCl$. Yield: 0.11 moles (70%)
TLC: Rf 0.19 (n-BuOH/acetic A./$H_2O$ 5:2:2)
Melting point 252–255° C.

EXAMPLE 5

Preparation of 1-(4-amino-6,7-dimethoxy-2-quinazolinyl)-4-(2-pyridyl)piperidine(hydrochloride)
(Compound 7 of Table 1)

20 g of 4-(2-pyridyl)-piperidine.2HCl (Compound D) (0.085 moles) were dissolved in 100 ml of $H_2O$. The solution was made alkaline with 50 ml of 2N NaOH and extracted by washing with two lots of 100 ml of ethyl acetate. The organic phases were pooled and evaporated to dryness, the oily residue was taken up in 300 ml of isoamyl alcohol to which were added 20.4 g of 2-chloro-4-amino-6,7-dimethoxy-quinazoline (0.085 moles). The mixture was heated to boiling point for 5 hours and, after cooling, the precipitate formed was filtered off and washed with acetone. 24 g of Compound 7 were obtained after drying.

Formula: $C_{20}H_{23}N_5O_2.HCl$. Yield: 0.06 moles (71%)
TLC: Rf 0.35 (n-BuOH/acetic A./$H_2O$ 5:2:2)

HPLC: (r.t.) 23.8 min (see note 2 of Table 1)

Melting point: 275.7° C. (as DSC)

All of the compounds of formula (I) were synthesised by the procedure described in Example 5, that is, by reacting 2-chloro-4-amino-6,7-dimethoxy-quinazoline with the appropriate piperidine of formula (II). Table 1, below, gives several derivatives of formula (I) according the invention obtained in this way together with some identifying physico-chemical characteristics, without this being limiting in any way of the spirit and scope of the invention itself.

TABLE 1

Compounds of formula (I)

(I)

| Compound | Formula | Ar | TLC[1] (r.f) | HPLC[2] (r.t) min | DSC[3] onset (° C.) |
|---|---|---|---|---|---|
| 1 | $C_{21}H_{24}N_4O_2 \cdot HCl$ | Phenyl | 0.71 | 12.3 | 291.9 |
| 2 | $C_{22}H_{26}N_4O_3 \cdot HCl$ | 2-methoxyphenyl | 0.74 | 14.8 | 297.3 |
| 3 | $C_{22}H_{28}N_4O_3 \cdot HCl$ | 2-ethoxyphenyl | 0.78 | 15.6 | 299.6 |
| 4 | $C_{19}H_{22}N_4O_2 \cdot HCl$ | 2-furyl | 0.82 | 10.1 | 287.3 |
| 5 | $C_{20}H_{24}N_4O_3 \cdot HCl$ | 2-(5-methylfuryl) | 0.80 | 12.2 | 274.1 |
| 6 | $C_{19}H_{22}N_4O_2S \cdot HCl$ | 2-thiophenyl | 0.71 | 11.7 | 291.5 |
| 7 | $C_{20}H_{23}N_5O_2 \cdot HCl$ | 2-pyridyl | 0.35 | 23.8 | 275.7 |
| 8 | $C_{23}H_{24}N_4O_3 \cdot HCl$ | 2-benzofuryl | 0.78 | 14.5 | 286.3 |
| 9 | $C_{23}H_{25}N_5O_2 \cdot HCl$ | 2-indolyl | 0.73 | 9.4 | 258.5 |
| 10 | $C_{25}H_{26}N_4O_2 \cdot HCl$ | 1-naphthyl | 0.77 | 17.3 | 311.9 |

Note:
[1]: Eluent: n-BuOH/Acetic A./$H_2O$(5/2/2:v/v)
[2]: Mobile phase: phosphate buffer + MeOH(25/75)/Acetonitrile (80/20:v/v) Stationary phase: Adsorbosphere C18
[3]: DSC = Differential calorimetric scan Table 2 gives some physico-chemical characteristics of the intermediate compounds of formula (II) obtained as previously described while, for those compounds already known, the respective "Chemical Abstract Registry Number" is also noted.

TABLE 2

Compounds of formula (II)

(II)

| Compound | Formula | Melting Point | TLC[1] (r.f) | Registry Number |
|---|---|---|---|---|
| 4-(2-pyridyl)-piperidine.2HCl[2] | $C_{10}H_{14}N_2 \cdot 2HCl$ | 252–255 | 0.19 | 30532-37-7 |
| 4-phenyl-piperidine | $C_{11}H_{15}N \cdot HCl$ | 286–287 | 0.64 | 771-99-3 |
| 4-(2-methoxyphenyl)-piperidine | $C_{12}H_{17}NO \cdot HCl$ | 258–260 | 0.71 | 58333-75-8 |
| 4-(2-ethoxyphenyl)-piperidine | $C_{13}H_{19}NO \cdot HCl$ | 250 | 0.80 | 100617-80-9 |

TABLE 2-continued

Compounds of formula (II)

(II)

| Compound | Formula | Melting Point | TLC[1] (r.f) | Registry Number |
|---|---|---|---|---|
| 4-(2-furyl)piperidine | $C_9H_{13}NO \cdot HCl$ | 151–152 | 0.64 | — |
| 4-(2-furyl-5methyl)-piperidine[3] | $C_{10}H_{15}NO$ | — | 0.71 | — |
| 4-(2-thiophenyl)-piperidine[3] | $C_9H_{13}NS$ | — | 0.52 | — |
| 4-(2-benzofuryl)-piperidine | $C_{13}H_{15}NO \cdot HCl$ | 235–236 | 0.56 | 54477-05-3 |
| 4-(3-indolyl)-piperidine[4] | $C_{13}H_{16}N_2$ | 224–226 | 0.55 | 17403-09-7 |
| 4-(2-naphthyl)-piperidine | $C_{15}H_{17}N \cdot HCl$ | 329[5] | 0.62 | — |

Note:
[1]: Eluent: n-BuOH/Acetic A./$H_2O$(5/2/2:v/v)
[2]: See Example 4
[3]: Utilized directly as bases and not isolated
[4]: Prepared in a similar way to DE3026365A
[5]: DSC onset

DESCRIPTION OF THE PHARMACOLOGICAL ACTIVITY

1) In Vitro Anti-adrenergic Activity (Alpha$_1$-antagonist)

In order to evaluate the affinity of the compounds of the invention towards the different alpha$_1$ adrenergic receptor subtypes, binding studies were made with the use of [$^3$H]-prazosin as a marked binder and rat submaxillary glands (GSM) as a tissue providing the alpha$_{1A}$ adrenergic receptor component, rat liver as the tissue providing the alpha$_{1B}$ adrenergic receptor component, and the human prostate as the tissue providing a mixed alpha$_{1A}$ and alpha$_{1C}$ component. It should, however, be noted that there is still some controversy relating to the classification of this receptor subtype which has, moreover, already been cloned [see, for example, Pimoule et al. Eur. J. Pharmacol. 290 (1995), 49–53, and Yamada et al., Life Sci. 54 (1994), 1845–1854].

a) In order to evaluate the binding of [$^3$H]-prazosin in the rat GSM, the method of Michel et al (Br.J. Pharmacol.) 88 (1989), 883–889, was used with slight modifications. Two symmetrical rat glands were used so as to obtain a final pellet having a proteinaceous concentration of approximately 400 μg/250 μl. The experimental conditions were: specific activity of the tracer: 74.4 Ci/mmole; incubation time 45 min (25° C.) TRIS+ EDTA buffer pH 7.4.

b) In order in to evaluate the binding of [$^3$H]-prazosin in the rat liver, Michel's previously cited method was used with the same experimental binding conditions. A final pellet having a proteinaceous concentration of approximately 600 μg/250 μl was used.

c) In order to evaluate the binding of [$^3$H]-prazosin in the human prostate, the method of Yamada et al was used (Life Sci.) 50 (1992), 127–135, with slight modifications. A final pellet having a proteinaceous concentration of approximately 350–400 μg/250 μl was obtained. Incubation time 30 min (25° C.); Tris+MgCl$_2$ buffer pH 7.5.

The results obtained with several of the compounds of the invention are listed in Table 3 which gives the IC$_{50}$ values, that is, the concentration (in nanomoles/liter) of antagonist capable of displacing 50% of the [$^3$H]-prazosin from the receptor.

TABLE 3

Inhibition of the binding of [$^3$H]-prazosin
($IC_{50} \times 10^{-9}$M) in:
rat submaxiliary glands (GSM) (alpha$_{1A}$ receptor subtype)
rat liver (alpha$_{1B}$ receptor subtype)
human prostate (alpha$_{1A}$ + alpha$_{1C}$ receptor subtype)

| Compound | rat GSM alpha$_{1A}$ subtype | rat liver alpha$_{1B}$ subtype | human prostate (alpha$_{1A}$ + alpha$_{1C}$) subtype |
|---|---|---|---|
| 1 | 6.1 | 13.0 | 2.0 |
| 2 | 18.8 | 7.7 | 7.8 |
| 3 | 10.7 | 14.0 | 10.8 |
| 4 | 3.1 | 1.7 | 3.8 |
| 5 | 3.5 | 2.1 | 1.7 |
| 6 | 4.1 | 6.0 | 4.5 |
| 7 | 3.1 | 8.2 | 5.0 |
| 8 | 18.4 | 5.2 | 20 |
| 9 | 5.7 | 2.9 | 2.5 |
| 10 | 88.0 | 62.0 | IN (>100) |
| Prazosin | 3.9 | 3.3 | 2.3 |
| WB-4101 | 16.5 | 12.0 | NT |
| Ketanserine | 48.2 | 29.9 | 270 |

NT: Not tested

From the data given in Table 3 it can be seen that many of the compounds of the invention are powerful antagonists of the alpha$_{1A}$, alpha$_{1B}$ and alpha$_{1C}$ adrenergic receptor subtypes. For example, the compounds 4, 5, 7 and 9 generally display an activity similar to that of prazosin, while the other two reference compounds chosen, WB-4101 [J. Med. Chem. 12, (1969), p. 326], a powerful alpha$_{1A}$ antagonist, and ketanserine, a powerful 5-HT$_2$ and alpha$_1$ adrenergic antagonist, this latter being used like prazosin in treating human hypertension, are on average approximately 10 to 30 times less powerful.

2) In Vitro Anti-serotinin Activity: Rabbit Aorta

The antagonist activity of some of the compounds of the invention on the contractile activity of seratonin on isolated rabbit aorta, effected principally by way of the 5-HT$_2$ receptors, is reported here by way of example. The method of Feniuk et al [Br. J. Pharmacol. (1985), 86, 697–704] was used, with slight modifications. Four rings formed from rabbit aorta were joined together to form a chain; the preparation was placed in an isolated organ bath in the presence of Krebs at 37° C. and attached to an isometric transducer, a tension of 2 g being applied and oxygenation was carried out continuously with $O_2$—$CO_2$ (95-5 v/v). A seratonin concentration(0.3 $\mu$M) was used that was capable of causing sub-maximal contraction of the preparation. The compound to be tested was administered 10 minutes before stimulation by the agonist; use of different concentrations of the drug enabled the determination of the IC$_{50}$ value, that is the concentration in $\mu$g/ml of drug capable of antagonising the contraction caused by the agonist by 50%. The results obtained in this way are given in Table 4 below which, for several of the compounds of the invention gives IC$_{50}$ values calculated by the regression method on a set of at least 2 experiments at 5 different concentrations for each of the compounds examined, these being compared with values obtained for several reference compounds.

TABLE 4

Inhibitory effect (IC$_{50}$ $\mu$g/ml) on the contraction caused by 0.3 $\mu$M seratonin in the smooth vasal musculature of isolated rabbit aorta

| Compound | IC$_{50}$ | (basal limits - p < 0.05) ($\mu$g/ml) |
|---|---|---|
| 1 | 6.0 | (4.6–7.8) |
| 2 | 14.7 | (9.5–22.6) |
| 3 | 30.0 | (17.2–52.5) |
| 4 | 11.6 | (5.6–23.9) |
| 5 | 3.1 | (2.2–4.1) |
| 6 | 32.7 | (25.4–42.1) |
| 7 | 20.0 | (10.8–37.4) |
| 8 | 6.7 | (4.3–10.4) |
| 9 | 13.0 | (8.4–19.9) |
| 10 | inactive (>50) | |
| Prazosin | inactive (>50) | |
| WB-4101 | inactive (>50) | |
| Ketanserine | 0.09 | (0.07–0.12) |

From the data given in Table 4 it can be seen that several of the compounds of the invention, in addition to their extremely powerful anti-adrenergic (alpha$_1$) activity previously described, also show strong 5-HT$_2$-antagonist activity. For example, Compound 5 has an IC$_{50}$ of 3.1 $\mu$g /ml (7.6 $\mu$M), which is approximately 30 times less than that of an extremely powerful and specific antagonist such as ketanserine (IC$_{50}$ 0.09 $\mu$g/ml). The other reference adrenergic antagonists examined such as prazosin and WB-4101 are found to be inactive until higher doses (50 $\mu$g/ml) are used.

3) Hypotensive Activity in the Anaesthetised Normotensive Rat

In order to evaluate the in vivo activity, some of the compounds of the invention were administered (IV) in bolus form to the normotensive rat anaesthetised with urethane plus ketamine. The compounds were administered in at least three doses in experiments performed in duplicate so as to enable the calculation of ED$_{30}$ values, that is, the dose in mg/kg that reduces the mean basal arterial pressure by 30%. The compounds of the invention, and several reference standards, were dissolved in dilute hydrochloric acid at a physiologically acceptable pH, and physiological solution was administered in a volume of 3 ml/kg. Evaluations were made at two time periods, that is, the intervals 0–30 min and 30–60 min after administration. The values obtained in this way are given in Table 5 below.

TABLE 5

Reduction in mean arterial pressure (ED$_{30}$ mg/kg) in the anaesthetised normotensive rat, caused by the IV administration in bolus form of the indicated compounds of the invention

| Compound | Interval 0–30 min | Interval 30–60 min |
|---|---|---|
| 1 | 0.19 | 0.31 |
| 2 | 0.50 | 0.55 |
| 3 | 0.32 | 0.35 |
| 4 | 0.08 | 0.10 |
| 5 | 0.03 | 0.03 |
| 6 | 0.06 | 0.08 |
| 7 | 0.08 | 0.09 |
| 8 | 0.07 | 0.09 |
| 9 | 0.10 | 0.19 |
| 10 | 1.00 | 1.83 |
| Prazosin | 0.02 | 0.05 |
| WB-4101 | 0.13 | 0.29 |
| Verapamil | 0.63 | 1.06 |

From the data given in the table, it can be seen that some of the compounds of the invention, such as compounds 4, 5, 6, 7 and 8, have a hypotensive activity similar to that of prazosin. The other two reference compounds used, Verapamil and WB-1401, are less active.

4) Anti-hypertensive Activity in the Spontaneously Hypertensive (SHR) Rat

Some of the compounds of the invention were administered orally to the SHR rat with the use of various concentrations of product so as to enable the calculation of $ED_{20}$ values, that is, the dose in mg/kg which causes a 20% reduction in the mean basal systolic pressure 0–120 min after administration. Animals having a mean basal systolic pressure of not less than 180 mmHg were used.

The values obtained in this way are shown in Table 6, which also gives the maximum effect on blood pressure caused by the 3 mg/kg dose for each product examined, as well as the effect of this dose on cardiac frequency.

TABLE 6

Reduction in systolic arterial pressure in the spontaneously hypertensive (SHR) rat induced by the oral administration of the indicated compounds of the invention

| | Systolic pressure | | Cardiac frequency |
|---|---|---|---|
| Compound | Max effect at 3 mg/kg % vs basal | $ED_{20}$ (0–120 min) (mg/kg) | Max effect at 3 mg/kg % vs basal |
| 1 | −7.5 | NC[1] | −0.8 |
| 2 | −6.4 | NC | +2.1 |
| 4 | −15.5 | 13.1 | +0.6 |
| 5 | −22.1 | 2.0 | −0.2 |
| 6 | −8.4 | NC | +2.7 |
| 7 | −22.7 | 2.2 | +0.9 |
| 8 | −20.2 | 2.6 | −5.2 |
| Prazosin | −20.0 | 2.8 | +9.7[2] |
| Verapamil | −9.0 | NC | +2.8 |
| WB-4101 | −2.6 | INACTIVE | −5.7 |

Note:
[1]: NC: not calculable
[2]: statistically significant (p < 0.05)

From the data given in the table, it can be inferred that many of the compounds of the invention display a powerful anti-hypertensive action in the spontaneously hypertensive rat.

Thus, for example, compounds 5, 7 and 8 are shown, in this experiment, to be about as powerful as prazosin, the reference alpha$_1$-adrenergic antagonist. In addition, in the range of doses tested, 0.3–10 mg/kg, the compounds of the invention do not appear to induce reflex tachycardia as a result of the reduction in pressure. However, prazosin, at the 3 mg/kg dose, produces a significant increase in frequency of approximately 10% over the basal frequency. Of the other two reference compounds tested, WB-4101 is inactive, probably because it is poorly absorbed by the oral route, while the calcium antagonist, verapamil, is less effective in that it does not reduce the arterial pressure by more than 9% at a dose of 3 mg/kg.

A further important and advantageous characteristic of the compounds of the invention is the high level of absorption that they show following oral administration, and their long half-lives. This is shown clearly by the data obtained with Compound 7, administered to the rat at 1 mg/kg IV and 15 mg/kg OS. These results are given in Table 7 below.

TABLE 7

Plasma concentration (μg/ml) of Compound 7 in the rat

| | Time (hours) | | | | | | | | | | | AUC (μg/ml-hour) |
|---|---|---|---|---|---|---|---|---|---|---|---|---|
| | 0.083 | 0.25 | 0.5 | 1 | 2 | 3 | 4 | 6 | 8 | 12 | 24 | |
| IV | 0.42 | 0.30 | 0.18 | 0.10 | 0.04 | 0.02 | 0.01 | 0 | — | — | — | 0.30 |
| OS | — | 0.23 | 0.36 | 0.48 | 0.39 | 0.34 | 0.32 | 0.28 | 0.18 | 0.08 | 0.02 | 3.62 |

From the data given it can be seen that the relative bioavailability of Compound 7 (that is, the ratio $AUC_{OS}/AUC_{IV}$), allowing for the corrections which are necessary to take account of the different doses used for the two routes of administration, is extremely high (approximately 80%).

The half-life calculated for the terminal elimination phase is also high (approximately 6 hours); much greater therefore than that reported in the literature for, for example, prazosin [approximately 2 hours—Martindale—29th Ed.—page 496]. This result shows that this and other compounds of the invention can, to advantage, be administered to humans in one or, at most, two daily doses.

We claim:

1. A compound represented by the general formula (I) indicated below

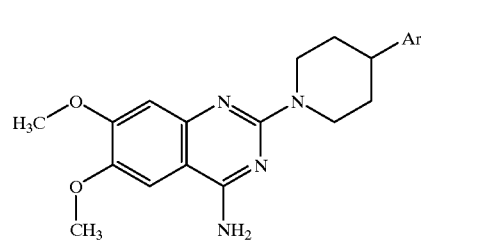

(I)

in which:
Ar is
  an unsubstituted pyridyl group (2-, 3- or 4-yl) or a pyridyl group mono-substituted with a methoxy or methyl group
  an unsubstituted furyl group (2- or 3-yl) or a furyl group substituted with a methoxy or methyl group, or
  a benzofuryl group (2- or 3-yl)
and its salts obtained from pharmaceutically acceptable inorganic or organic acids.

2. A compound according to formula (I) of claim 1, in which Ar is an unsubstituted pyridyl group (2-, 3- or 4-yl) or a pyridyl group mono-substituted with a methoxy or methyl group, and its pharmaceutically acceptable salts.

3. A Compound according to claim 2, in which Ar is the 2-pyridyl group, and its pharmaceutically acceptable salts.

4. A compound according to formula (I) of claim 1, in which Ar is an unsubstituted furyl group (2- or 3-yl) or a furyl group substituted with a methoxy or methyl group, and its pharmaceutically acceptable salts.

5. A compound according to claim 4, in which Ar is a 2-furyl group, and its pharmaceutically acceptable salts.

6. A pharmaceutical preparation comprising, as an active ingredient, at least one of the compounds according to claim 1, or a pharmaceutically acceptable salt thereof, and a pharmaceutically acceptable inactive ingredient.

7. A pharmaceutical preparation according to claim 6, wherein the pharmaceutically acceptable inactive ingredient is selected from the group consisting of vehicles, binders, aromatisers, dispersants, preservatives, humectants, and mixtures thereof, ingredients which facilitate transdermal absorption, and ingredients which enable the controlled release of the active ingredient over time.

8. A method for treating arterial hypertension of diverse etiology comprising administering an effective amount of a pharmaceutical preparation according to claim 6 to a patient in need thereof.

9. A method for treating prostate hypertrophy comprising administering an effective amount of a pharmaceutical preparation according to claim 6 to a patient in need thereof.

10. A method for preparing a compound of formula (I), or a pharmaceutically acceptable salt thereof, as claimed in claim 1, which comprises reacting a piperidine derivative of formula (II):

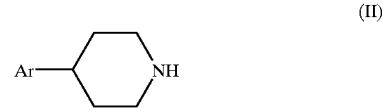

(II)

in which Ar is defined in claim 1, with 2-Cl-4-amino-6,7-dimethoxy-quinazoline in a high boiling solvent, in the presence or absence of a tertiary base as a proton acceptor, at a temperature of 70–150° C. for 1–48 hours, and isolating a compound of formula (I) from the reaction medium by filtration either as such, or in the form of a pharmaceutically acceptable salt.

11. A method according to claim 10, wherein said high boiling solvent is isoamyl alcohol.

12. A method according to claim 10, wherein the compound of formula (I) is isolated in the form of its pharmaceutically acceptable salt.

* * * * *